(12) United States Patent
Xu

(10) Patent No.: US 9,974,842 B2
(45) Date of Patent: May 22, 2018

(54) INOTROPIC ANTIBODIES AND THERAPEUTIC USES THEREOF

(71) Applicant: Kai Yuan Xu, Cockeysville, MD (US)

(72) Inventor: Kai Yuan Xu, Cockeysville, MD (US)

( * ) Notice: Subject to any disclaimer, the term of this patent is extended or adjusted under 35 U.S.C. 154(b) by 255 days.

(21) Appl. No.: 15/062,329

(22) Filed: Mar. 7, 2016

(65) Prior Publication Data
US 2016/0199468 A1   Jul. 14, 2016

Related U.S. Application Data

(62) Division of application No. 14/574,310, filed on Dec. 17, 2014, now Pat. No. 9,279,020, which is a division of application No. 13/765,367, filed on Feb. 12, 2013, now Pat. No. 8,945,555, which is a division of application No. 12/750,617, filed on Mar. 30, 2010, now Pat. No. 8,383,111, which is a division of application No. 10/607,583, filed on Jun. 25, 2003, now Pat. No. 7,754,210.

(60) Provisional application No. 60/456,879, filed on Mar. 21, 2003.

(51) Int. Cl.
*A61K 38/00* (2006.01)
*A61K 39/00* (2006.01)
*C07K 16/40* (2006.01)
*A61K 48/00* (2006.01)

(52) U.S. Cl.
CPC .......... *A61K 39/0005* (2013.01); *C07K 16/40* (2013.01); *A61K 48/00* (2013.01); *C07K 2317/34* (2013.01); *C07K 2317/75* (2013.01)

(58) Field of Classification Search
None
See application file for complete search history.

(56) References Cited

PUBLICATIONS

Arystarkova (1992) JBC 267: 13694-13701.*

* cited by examiner

*Primary Examiner* — Michael D Pak

(57) ABSTRACT

Antibodies binding to sites on the alpha-subunit of the $(Na^+ + K^+)$-ATPase increase cardiac contraction of both ventricular myocytes and mouse heart. In particular, antibodies binding to the RSATEEEPPNDD (SEQ ID NO: 1) or DVEDSYGQQTYEQR (SEQ ID NO: 2) peptides (or isoforms/derivatives thereof) of the alpha-subunit of the $(Na^+ + K^+)$-ATPase, have been found to be highly inotropic. Both the antibodies and the peptides are important for the treatment of human heart failure and other contractile disorders.

3 Claims, 7 Drawing Sheets

INOTROPIC ANTIBODIES AND THERAPEUTIC USES THEREOF

This is a divisional application of prior application Ser. No. 10/607,583 Filed on Jun. 25, 2003, Ser. No. 12/750,617 filed on Mar. 30, 2010, Ser. No. 13/765,367 filed on Feb. 12, 2013, and Ser. No. 14/574,310 on Dec. 17, 2014, which claims the benefit of U.S. provisional application No. 60/391,514 filed Jun. 25, 2002 and U.S. provisional application No. 60/456,879 filed Mar. 21, 2003, both of which are hereby incorporated by reference herein in their entirety.

FIELD OF THE INVENTION

Structural regions of the $(Na^++K^+)$-ATPase that are directly involved in the regulation of cardiac contractility are provided. Site-specific binding of these antibodies against the known sequences of the $(Na^++K^+)$-ATPase significantly increased cardiac contraction of both isolated rat cardiac myocytes and mouse hearts. These important findings provide functional connection between the structure of the $(Na^++K^+)$-ATPase and cardiac positive inotropy, wherein a novel mode for $(Na^++K^+)$-ATPase to regulate cardiac function is shown.

BACKGROUND $(Na^++K^+)$-ATPase is a target receptor for digitalis and related drugs. Digitalis, digoxin, ouabain and related substances are cardiac glycosides derived from plants. The main pharmacodynamic property of cardiac glycosides is the ability to increase the force of myocardial contraction in a dose-dependent manner (positive inotropic effect). The most probable explanation for the direct positive inotropic effect is the ability of cardiac glycosides to inhibit membrane-bound $(Na^++K^+)$-activated adenosine triphosphatase [$(Na^++K^+)$-ATPase](Hoffman, B. F. and J. T. Bigger, Jr., "Digitalis and Allied Cardiac Glycosides" in The Pharmacological Basis of Therapeutics, eds. Goodman and Gilman, p. 732, (1980)). The hydrolysis of adenosine triphosphate (ATP) by this enzyme provides the energy for the sodium potassium pump.

The precise structural region of $(Na^++K^+)$-ATPase that regulates cardiac function is not well understood. Hence, relatively little is known about the endogenous regulation of $(Na^++K^+)$-ATPase. Catecholamines (Phillis, J. W., Cell, Tissue and Organ Cultures in Neurobiology, pp. 93-97 (1978); Horwitz, B. A., Fed Proc., 38:2170-2176 (1979)), thyroid hormone (Smith, T. J. and I. S. Edelman, Fed. Proc., 38:2150-2153 (1979)), aldosterone (Rossier, B. C., et al., Science, 12:483-487 (1987)), linoleic and linolenic acids (Bidard, J. N., et al., Biochem. Biophys. Acta., 769:245 (1984); Tamura, M., et al., J. Biol. Chem., 260:9672 (1985); and vanadium (Cantley, L. C., Jr., et al., J. Biol. Chem., 243:7361-7368 (1978)) have all been linked to either direct or indirect effects on enzyme activity.

Because of their positive inotropic effect, cardiac glycosides (e.g., digitalis and ouabain) are unrivaled in value for the treatment of heart failure. Cardiac glycosides are most frequently used therapeutically to increase the adequacy of the circulation in patients with congestive heart failure and to slow the ventricular rate in the presence of atrial fibrillation and flutter.

However, cardiac glycosides have narrow therapeutic indices and their use is frequently accompanied by toxic effects that can be severe or lethal. The most important toxic effects, in terms of risk to the patient, are those that involve the heart (e.g., abnormalities of cardiac rhythm and disturbances of atrio-ventricular conduction). Gastrointestinal disorders, neurological effects, anorexia, blurred vision, nausea and vomiting are other common cardiac glycoside-induced reactions. Consequently, there is a need in the art for positive inotropic agents which overcome the disadvantages associated with known agents, as well as a need for further information on the mechanisms and receptors associated with cardiac muscle contractility.

It would be highly beneficial to provide patients with a therapeutic composition wherein the cardiac regulatory functions of $(Na^++K^+)$-ATPase are specifically regulated. Moreover, the identification of the key structural regions and amino acids of the $(Na^++K^+)$-ATPase would be of great importance in developing more specific therapeutic molecules, which specifically regulate the cardiac function and differ in characteristics from currently available digitalis glycosides.

SUMMARY OF THE INVENTION

The present invention provides for the identification of the key functional sites of $(Na^++K^+)$-ATPase and also of inotropic agents which directly participate in the regulation of cardiac contraction. In particular, the inotropic agents are antibodies which bind to these functional sites (epitopes) in the alpha-subunit of $(Na^++K^+)$-ATPase and induce a positive inotropic effect.

In particular, the invention provides for isolated and/or purified antibodies (including both exogenous and endogenous) which bind to the structural binding site of $(Na^++K^+)$-ATPase and regulate $(Na^++K^+)$-ATPase functions. This is of importance in the treatment of heart disease and other muscle contraction diseases. The antibodies of the invention are polyclonal and/or antisera, monoclonal, and/or humanized antibodies.

The invention also provides for isolated and/or purified antibodies (including both exogenous and endogenous) which specifically recognize the amino acid sequences comprising RSATEEEPPNDD (SEQ ID NO; 1) and/or DVEDSYGQQWTYEQR (SEQ ID NO; 1) of the alpha-subunit of $(Na^++K^+)$-ATPase enzyme. The binding of the antibodies to these amino acid sequences of the alpha-subunit of $(Na^++K^+)$-ATPase increase cardiac contraction and myocyte intracellular diastolic and systolic calcium Preferred antibodies of the invention exert a positive inotropic effect in cardiac myocytes, when they bind to their specific epitopes in the alpha-subunit of $(Na^++K^+)$-ATPase. The antibodies can be from antisera, polyclonal, monoclonal, and/or humanized antibodies. In a preferred embodiment the antibodies of the invention are used as a therapeutic agent to treat patients suffering from or susceptible to heart disease and/or other muscle contraction disorders.

In particular, the invention provides for purified peptides which are used to generate inotropic antibodies when administered in vivo to a patient, suffering from or susceptible to heart disease and/or muscle contractile disorders. These peptides can be administered individually or in combination in a pharmaceutically acceptable carrier to a patient.

The invention also provides for isolated and/or purified peptides comprising the amino acid sequence RSATEEEP-PNDD (SEQ ID NO; 1) and DVEDSYGQQWTYEQR (SEQ ID NO; 2) or derivatives thereof (including isoforms), which are used to generate inotropic antibodies when administered in vivo to a patient suffering from or susceptible to heart disease and/or myocyte contractile disorders. These peptides can be administered individually or in combination in a pharmaceutically acceptable carrier to a patient. Preferred isoforms of such peptides (i.e. comprising the sequence RSATEEEPPNDD (SEQ ID NO; 1) or DVEDSYGQQWTYEQR) (SEQ ID NO; 2) will also will generate such antibodies and preferably will comprise an amino acid sequence that has only 1, 2, 3, 4, 5, 6, 7 or 8 total amino acid differences from the sequence of RSATEEEP-PNDD (SEQ ID NO; 1) or DVEDSYGQQWTYEQR, (SEQ ID NO; 2) more preferably will comprise an amino acid sequence that has only 1, 2, 3, or 4 total amino acid differences from the sequence of RSATEEEPPNDD (SEQ ID NO; 1) or DVEDSYGQQWTYEQR (SEQ ID NO; 2).

In accordance with the invention the peptides can be administered in concentrations in a ratio of 1:1 or in varying ratios to each other as defined by their concentration.

In another preferred embodiment, the invention provides for vectors which encode amino acid sequences which are used to generate inotropic antibodies when administered in vivo to a patient suffering from or susceptible to heart disease and/or myocyte contractile disorders. Preferably these vectors are under the control of tissue specific promoters, in particular, cardiac tissue specific. These vectors are also preferably used in generating sera comprising inotropic antibodies using standard methods such as immunizing mammals.

In another preferred embodiment, the invention provides for vectors which encode the amino acid sequences RSATEEEPPNDD (SEQ ID NO: 1), DVEDSYGQQWTV-VYEQR (SEQ ID NO: 2) or isoforms (derivatives) thereof, are used to generate inotropic antibodies when administered in vivo to a patient suffering from or susceptible to heart disease and/or myocyte contractile disorders. Preferably these vectors are under the control of tissue specific promoters, in particular, cardiac tissue specific. These peptides are administered as a vaccine to a patient in need of such therapy, in order to generate endogenous inotropic antibodies.

The amino acids which are encoded by the vector stimulate the immune system to generate antibodies which bind to their epitopes in the alpha-subunit of $(Na^++K^+)$-ATPase, resulting in increased myocyte intracellular diastolic and systolic calcium. These antibodies, exert a positive inotropic effect in cardiac.

In a preferred embodiment, the invention provides for the therapeutic use of antisera, polyclonal and monoclonal antibodies and/or humanized antibodies that specifically bind to amino acid sequences of $(Na^++K^+)$-ATPase enzyme and modulate the activity of the enzyme, for treating patients suffering from or susceptible to heart disease and/or muscle contractile disorders. These antibodies are also used to block other molecules from binding to drug-interaction sites so that a patient suffering from heart disorders such as, for example, arhythmia, tachyrhithmia and the like, are useful in regulating cardiac contraction. The antibodies in this case would also function to eliminate of certain precipitating drugs, including negative inotropic agents (e.g., certain calcium channel blockers and antiarrhythmic drugs like disopyramide), cardiotoxins (e.g., amphetamines) and plasma volume expanders (e.g., nonsteroidal antiinflammatory agents and glucocorticoids).

In another preferred embodiment, the invention provides for a method of generating antibodies, wherein binding of the antibodies to an epitope of the alpha-subunit of $(Na^++K^+)$-ATPase exerts a positive inotropic effect in cardiac myocytes, comprising:
generating amino acid sequences corresponding to overlapping peptide fragments, and variants thereof, of the alpha-subunit of $(Na^++K^+)$-ATPase (including the alpha-subunit of one or more isoforms of $(Na^++K^+)$-ATPase); and,
obtaining antibodies specific for each peptide fragment by standard methods; and,
determining the effects of the antibodies on intracellular diastolic and systolic calcium levels and cell shortenings as compared to controls.

The antibodies produced by this method, when they bind to their antigenic sites in the alpha-subunit of $(Na^++K^+)$-ATPase (including the alpha-subunit of one or more isoforms of $(Na^++K^+)$-ATPase) exert a positive inotropic effect in cardiac myocytes. The antibodies can be from antisera, polyclonal antibodies, monoclonal antibodies, and/or humanized antibodies. These antibodies are also used in immunoassays (e.g. RIA, ELISA, etc.) for diagnosing different heart and contractile disorders.

In another preferred embodiment, the invention provides for a method for diagnosing heart failure and/or contractile disorders comprising:
isolating heart tissue using standard methods; and,
obtaining cell cultures from the heart tissue using standard methods; and,
allowing the binding of inotropic antibodies to specific epitopes; and,
measuring intracellular diastolic and systolic calcium and cell shortenings.

Preferably, the molecules of the invention are administered to a patient in an effective therapeutic amount to treat the patient suffering from or susceptible to heart disease and/or muscle contractile disorders.

In another preferred embodiment, the antibodies are administered to a patient (e.g. as a vaccine-type agent or inotrpoic reagent) in a therapeutically effective amount to block other molecules from binding to drug-interaction sites of $(Na^++K^+)$-ATPase, wherein the patient is suffering from or susceptible to arhythmias, tachyrhithmias and the like.

The invention also provides for identifying molecules which target and block the RSATEEEPPNDD (SEQ ID NO:1) and/or DVEDSYGQQWTYEQR (SEQ ID NO:2) (or isoforms/derivatives thereof) site of alpha-subunit of the $(Na^++K^+)$-ATPase (including the alpha-subunit of one or more isoforms of $(Na^++K^+)$-ATPase), comprising:
contacting a myocyte with a desired molecule; and,
measuring the intracellular diastolic and systolic $Ca^{2+}$; and,
measuring cell shortening and heart function; whereby,
identifying molecules useful for therapy of patients suffering from or susceptible to heart disease and other contractile disorders.

Such molecules are used to generate inotropic antibodies and/or generate peptide-based vaccines as therapeutic agents in patients suffering from and/or susceptible to heart disease and other contractile disorders.

The Jianye-2 peptide (comprising or consisting of sequence RSATEEEPPNDD) (SEQ ID NO:1)) as disclosed herein is a particularly preferred peptide. Isoforms (e.g. differing in sequence by 1, 2, 3, 4, 5, 6, 7, 8, 9 or 10 amino acids, preferably 1, 2, 3, 4, 5, 6, 7 or 8 amino acid differences, more preferably 1, 2, 3, or 4 amino acid differences) of the Jianye-2 peptide also are preferred and those amino acid differences may reflect differences among species.

The KX-1 peptide (comprising or consisting of sequence DVEDSYGQQWTYEQR (SEQ ID NO:2)) as disclosed herein is a further particularly preferred peptide. Isoforms (e.g. differing in sequence by 1, 2, 3, 4, 5, 6, 7, 8, 9 or 10 amino acids, preferably 1, 2, 3, 4, 5, 6, 7 or 8 amino acid differences, more preferably 1, 2, 3, or 4 amino acid differences) of the KX-1 peptide also are preferred and those amino acid differences may reflect differences among species.

Also preferred are antibodies and vaccines made against a region of the H1-H2 domain of the (Na$^+$+K$^+$)-ATPase (such as the Jianye-2 peptide or isoform thereof).

Additionally preferred are antibodies and vaccines made against a region of the H7-H8 domain of the (Na$^+$+K$^+$)-ATPase (such as the KX-1 peptide or isoform thereof).

Other aspects of the invention are described infra.

DEFINITIONS

As used herein, "inotropic agents" or "inotropic antibodies" will be used interchangeably and refers to the effect such agents produce, i.e. improves cardiac output by increasing the force of myocardial muscle contraction. "Positive inotropic effect" means that the contractility of the cells is enhanced in a dose-dependent manner. A positive inotropic effect-producing amount of antibodies or peptides of the invention can be administered to a "mammalian host" (e.g., a human) to treat cardiac malfunction (e.g., congestive heart failure, paroxysmal atrial tachycardia, atrial fibrillation and flutter). Administration can be either enteral (i.e., oral) or parenteral (e.g., via intravenous, subcutaneous or intramuscular injection).

As used herein, a "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. The invention also provides for vectors which are used for treating a patient suffering from or susceptible heart disease. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector.

Such components can be provided as a natural feature of the vector (such as the use of certain viral vectors which have components or functionalities mediating binding and uptake), or vectors can be modified to provide such functionalities. A large variety of such vectors are known in the art and are generally available.

As used herein, the term "administering a molecule to a cell" (e.g., an expression vector, nucleic acid, peptide, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10).

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

A "recombinant viral vector" refers to a viral vector comprising one or more heterologous genes or sequences. Since many viral vectors exhibit size-constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation) (see, e.g., the references and illustrations below). Modified viral vectors in which a polynucleotide to be delivered is carried on the outside of the viral particle have also been described (see, e.g., Curiel, D T, et al. PNAS 88: 8850-8854, 1991).

Viral "packaging" as used herein refers to a series of intracellular events that results in the synthesis and assembly of a viral vector. Packaging typically involves the replication of the "pro-viral genome", or a recombinant pro-vector typically referred to as a "vector plasmid" (which is a recombinant polynucleotide than can be packaged in an manner analogous to a viral genome, typically as a result of being flanked by appropriate viral "packaging sequences"), followed by encapsidation or other coating of the nucleic acid. Thus, when a suitable vector plasmid is introduced into a packaging cell line under appropriate conditions, it can be replicated and assembled into a viral particle. Viral "rep" and "cap" genes, found in many viral genomes, are genes encoding replication and encapsidation proteins, respectively. A "replication-defective" or "replication-incompetent" viral vector refers to a viral vector in which one or more functions necessary for replication and/or packaging are missing or altered, rendering the viral vector incapable of initiating viral replication following uptake by a host cell. To produce stocks of such replication-defective viral vectors, the virus or pro-viral nucleic acid can be introduced into a "packaging cell line" that has been modified to contain genes encoding the missing functions which can be supplied in trans).

For example, such packaging genes can be stably integrated into a replicon of the packaging cell line or they can be introduced by transfection with a "packaging plasmid" or helper virus carrying genes encoding the missing functions.

A "detectable marker gene" is a gene that allows cells carrying the gene to be specifically detected (e.g., distinguished from cells which do not carry the marker gene). A large variety of such marker genes are known in the art. Preferred examples thereof include detectable marker genes which encode proteins appearing on cellular surfaces, thereby facilitating simplified and rapid detection and/or cellular sorting. By way of illustration, the lacZ gene encoding beta-galactosidase can be used as a detectable marker, allowing cells transduced with a vector carrying the lacZ gene to be detected by staining, as described below.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., WO 92/08796, published May 29, 1992, and WO 94/28143, published Dec. 8, 1994). Such marker genes can provide an added measure of control that can be advantageous in gene therapy contexts. "Treatment" or "therapy" as used herein also refers to administering, to an individual patient, agents that are capable of eliciting a prophylactic, curative or other beneficial effect in the individual.

"Gene therapy" as used herein refers to administering, to an individual patient, vectors comprising a therapeutic gene.

A "therapeutic polynucleotide" or "therapeutic gene" refers to a nucleotide sequence that is capable, when transferred to an individual, of eliciting a prophylactic, curative or other beneficial effect in the individual.

The term "treatment" or grammatical equivalents encompasses the improvement and/or reversal of the symptoms of heart failure (i.e, the ability of the heart to pump blood). "Improvement in the physiologic function" of the heart can be assessed using any of the measurements described herein (e.g., measurement of ejection fraction, fractional shortening, left ventricular internal dimension, heart rate, etc. in response to isoproterenol and/or norepinephrine), as well as any effect upon the patient's survival. A compound which causes an improvement in any parameter associated with heart failure when used in the screening methods of the instant invention may thereby be identified as a therapeutic compound.

The term "individual" as used herein refers to vertebrates, particularly members of the mammalian species and includes but is not limited to, domestic animals, sports animals, primates and humans; more particularly, the term refers to humans.

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

As used herein, "contractile disorders" refers to the abnormal contractile response of muscle cells as compared to normal muscle cells. Examples of such disorders are arhythmia, tachyrhithmia, and the like.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides.

"Recombinant," as applied to a polynucleotide, means that the polynucleotide is the product of various combinations of cloning, restriction and/or ligation steps, and other procedures that result in a construct that is distinct from a polynucleotide found in nature.

A "gene" refers to a polynucleotide or portion of a polynucleotide comprising a sequence that encodes a protein. For most situations, it is desirable for the gene to also comprise a promoter operably linked to the coding sequence in order to effectively promote transcription. Enhancers, repressors and other regulatory sequences may also be included in order to modulate activity of the gene, as is well known in the art. (See, e.g., the references cited below).

The terms "polypeptide," "peptide," and "protein" are used interchangeably to refer to polymers of amino acids of any length. These terms also include proteins that are post-translationally modified through reactions that include glycosylation, acetylation and phosphorylation.

The terms "variant", "derivative" and "amino acid sequence variant" are used interchangeably and designate polypeptides in which one or more amino acids are added and/or substituted and/or deleted and/or inserted at the N- or C-terminus or anywhere within the corresponding native sequence. In various embodiments, a "variant" polypeptide usually has at least about 75% amino acid sequence identity, or at least about 80% amino acid sequence identity, preferably at least about 85% amino acid sequence identity, even more preferably at least about 90% amino acid sequence identity, and most preferably at least about 95% amino acid sequence identity with the amino acid sequence of the corresponding native sequence polypeptide.

An "effective amount" is an amount sufficient to effect beneficial or desired clinical results. An effective amount can be administered in one or more administrations. The antibodies, peptides or vectors used as vaccines of the present invention can be administered to a patient at therapeutically effective doses to treat (including prevention) heart disease and/or other muscular contractile disorders. A therapeutically effective dose refers to that amount of the compound sufficient to result in desired treatment.

As used herein, the term "fragment or segment", as applied to a polypeptide, will ordinarily be at least about 5 contiguous amino acids, typically at least about 10 contiguous amino acids, more typically at least about 20 contiguous amino acids, usually at least about 30 contiguous amino acids, preferably at least about 40 contiguous amino acids, more preferably at least about 50 contiguous amino acids, and even more preferably at least about 60 to 80 or more contiguous amino acids in length. "Overlapping fragments" as used herein, refer to contiguous peptide fragments which begin at the amino terminal end of a protein and end at the carboxy terminal end of the protein. Each peptide fragment has at least about one contiguous amino acid position in common with the next peptide fragment, more preferably at least about three contiguous amino acid positions in common, most preferably at least about ten contiguous amino acid positions in common.

As used herein, the term "substantially pure" describes a compound (e.g., a protein or polypeptide) which has been separated from components which naturally accompany it. Typically, a compound is substantially pure when at least 10%, more preferably at least 20%, more preferably at least 50%, more preferably at least 60%, more preferably at least 75%, more preferably at least 90%, and even more preferably at least 99%, of the total material (by volume, by wet or dry weight, or by mole percent or mole fraction) in a sample is the compound of interest. Purity can be measured by any appropriate method. In the case of polypeptides, for example, purity can be measured by column chromatography, polyacrylamide gel electrophoresis, or HPLC analysis. A compound such as a protein is also substantially purified when it is essentially free of naturally associated components or when it is separated from the native contaminants which accompany it in its natural state.

A "heterologous" component refers to a component that is introduced into or produced within a different entity from that in which it is naturally located. For example, a polynucleotide derived from one organism and introduced by genetic engineering techniques into a different organism is a heterologous polynucleotide which, if expressed, can encode a heterologous polypeptide. Similarly, a promoter or enhancer that is removed from its native coding sequence and operably linked to a different coding sequence is a heterologous promoter or enhancer.

A "substantially pure nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment such as the sequences adjacent to the fragment in a genome in which it naturally occurs. The term also applies to nucleic acids which have been substantially purified from other components which naturally accompany the nucleic acid, e.g., RNA or DNA, which has been purified from proteins which naturally accompany it in the cell.

"Homologous", as used herein, refers to the subunit sequence similarity between two polymeric molecules, e.g., between two nucleic acid molecules such as two DNA molecules, or two polypeptide molecules. When a subunit position in both of the two molecules is occupied by the same monomeric subunit (e.g., if a position in each of two DNA molecules is occupied by adenine) then they are homologous at that position. The homology between two sequences is a direct function of the number of matching or homologous positions. For example, if 5 of 10 positions in two compound sequences are matched or homologous then the two sequences are 50% homologous, if 9 of 10 are matched or homologous, the two sequences share 90% homology. By way of example, the DNA sequences 3' ATTGCC 5' and 3' TTTCCG 5' share 50% homology.

A "promoter," as used herein, refers to a polynucleotide sequence that controls transcription of a gene or coding sequence to which it is operably linked. A large number of promoters, including constitutive, inducible and repressible promoters, from a variety of different sources, are well known in the art and are available as or within cloned polynucleotide sequences (from, e.g., depositories such as the ATCC as well as other commercial or individual sources).

An "enhancer," as used herein, refers to a polynucleotide sequence that enhances transcription of a gene or coding sequence to which it is operably linked. A large number of enhancers, from a variety of different sources are well known in the art and available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences. "Operably linked" refers to a juxtaposition, wherein the components so described are in a relationship permitting them to function in their intended manner. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence.

A "replicon" refers to a polynucleotide comprising an origin of replication which allows for replication of the polynucleotide in an appropriate host cell. Examples include replicons of a target cell into which a heterologous nucleic acid might be integrated (e.g., nuclear and mitochondrial chromosomes), as well as extrachromosomal replicons (such as replicating plasmids and episomes).

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab).sub.2, and F(ab').sub.2 fragments.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., Nature 256:495-497, 1975, and U.S. Pat. No. 4,376,110.

As used herein, an "antigenic determinant" is the portion of an antigen molecule that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by H. Mario Geysen et al. 1984. Proc. Natl. Acad. Sci. U.S.A. 81:3998-4002; PCT Publication No. WO 84/03564; and PCT Publication No. WO 84/03506.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

"Immunoassay" is an assay that uses an antibody to specifically bind an antigen (e.g., a marker). The immunoassay is characterized by the use of specific binding properties of a particular antibody to isolate, target, and/or quantify the antigen.

BRIEF DESCRIPTION OF FIGURES

FIGS. 1A-1B are photographs of the confocal image of rat cardiac myocytes in the presence of Jianye-2 (FIG. 1A) or with both Jianye-2 antibody and peptide blocker (FIG. 1B). FIG. 1C shows the immunofluorescent stainings of Jianye-2 antibody in a group of CV-1 cells at a magnification of 400.times. FIG. 1D is a photograph of a single CV-1 cell image at 3000.times. FIGS. 1E-1F are photographs showing Jianye-2 antibody staining in the presence of either 1 mM ouabain (FIG. 1E) or strophanthidin (FIG. 1F). The results indicate that Jianye-2 antibody binds to its antigenic site of the $(Na^++K^+)$-ATPase on the surface of the cell membrane.

DETAILED DESCRIPTION OF THE INVENTION

Figure 1:
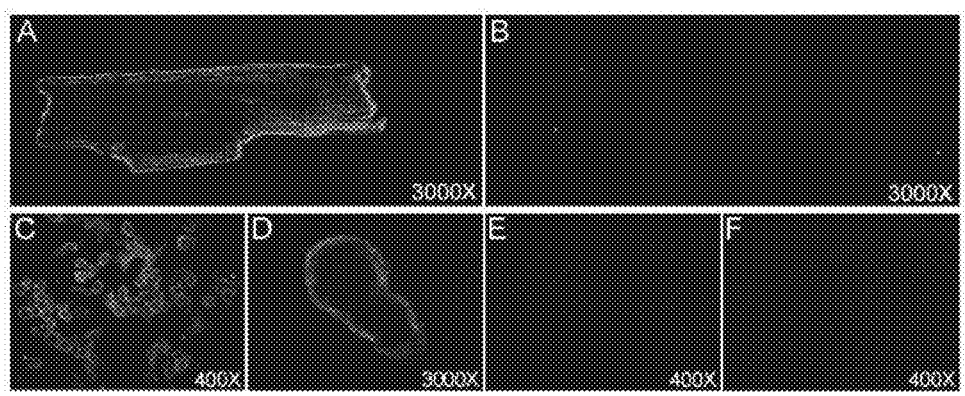
FIG. 1 (which includes FIGS. 1A through 1F) are photographs showing the immunofluorescent staining of Jianye-2 antibody in rat cardiac myocytes and African green monkey CV-1 cells.

Antibody (Jianye-2 antibody), which recognizes the RSA-TEEEPPNDD (SEQ ID NO: 1) peptide (H1-H2 domain) of the alpha-subunit of the $(Na^++K^+)$-ATPase, and KX-1 antibody which recognizes the DVEDSYGQQWTYEQR (SEQ ID NO: 2) peptide (H7-H8 domain) of the alpha-subunit of the $(Na^++K^+)$-ATPase, have been found to increase the contractility of ventricular myocytes which is important in the treatment of muscle contractile disorders.

In a preferred embodiment, the invention provides for antisera, polyclonal and monoclonal antibodies and/or humanized antibodies that specifically bind to amino acid sequences of $(Na^++K^+)$ATPase, resulting in increased intracellular $Ca^{2+}$ transients and contraction in intact mammalian heart cells and in living mouse heart.

In accordance with the invention, it is preferred that the antibodies specifically bind to peptides having an amino acid sequence RSATEEEPPNDD (SEQ ID NO: 1) (the antibody is referred to herein as the "Jianye-2" antibody), and DVEDSYGQQWTYEQR (SEQ ID NO: 2) (the antibody referred to herein as the "KX-1" antibody), mutants or derivatives thereof. These peptides can be conjugated into polypeptides either directly or through a linker. However, the invention is not limited to these sequences but applies to any sequence in which antibodies can bind resulting in cardiac positive inotropy. The Jianye-2 and KX-1 antibodies are described in detail in the Examples which follow.

In a preferred embodiment, the invention provides for the therapeutic use of antisera, polyclonal and monoclonal antibodies and/or humanized antibodies that specifically bind to amino acid sequences of $(Na^++K^+)$-ATPase enzyme and modulate the activity of the enzyme, for treating patients suffering from or susceptible to heart disease and/or muscle contractile disorders. These antibodies are also used to block other molecules from binding to drug-interaction sites so that a patient suffering from heart disorders such as, for example, arhythmia, tachyrhithmia and the like, are useful in regulating cardiac contraction. The antibodies in this case would also function to eliminate of certain precipitating drugs, including negative inotropic agents (e.g., certain calcium channel blockers and antiarrhythmic drugs like disopyramide), cardiotoxins (e.g., amphetamines) and plasma volume expanders (e.g., nonsteroidal antiinflammatory agents and glucocorticoids).

In another preferred embodiment, antibodies that bind to specific sequences of $(Na^++K^+)$-ATPase and can produce cardiac positive inotropy are administered to patients in need of such therapy.

In another embodiment, the molecules of the invention are used as diagnostic agents for heart disease or other contractile disorders, by detecting, in standard assays, such as ELISAs, RIAs and the like, peptides which are indicative of contractile disorders.

In another preferred embodiment, the invention provides for pharmaceutical compositions comprising peptides which are administered to patients resulting in the generation of antibodies which recognize such peptides resulting in the in vivo generation of inotropic antibodies. Particularly preferred peptides include, but are not limited to peptides with amino acid sequence RSATEEEPPNDD (SEQ ID NO: 1) and/or DVEDSYGQQWTYEQR (SEQ ID NO: 2), mutants and variants thereof.

In another preferred embodiment, the invention provides for a vaccine which codes for amino acids which generate inotropic antibodies when administered in vivo to a patient in need of such therapy or treatment.

In accordance with the invention, the antibodies of the invention are also used as diagnostic agents which detect muscle contractile disorders, especially, for example, in the heart. In one embodiment, any of the above-described molecules can be labeled, either detectably, as with a radioisotope, a paramagnetic atom, a fluorescent moiety, an enzyme, etc. in order to facilitate its detection in, for example, in situ or in vivo assays. The molecules may be labeled with reagents such as biotin, in order to, for example, facilitate their recovery, and/or detection.

In another preferred embodiment, where the antibodies or their fragments are intended for therapeutic purposes, it is desirable to "humanize" them in order to attenuate any immune reaction. Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041-1043 (1988); Liu, A. Y. et al. Proc. Natl. Acad. Sci. USA 84:3439-3443 (1987); Liu, A. Y. et al., J. Immunol. 139:3521-3526 (1987); Sun, L. K. et al., Proc. Natl. Acad. Sci. USA 84:214-218 (1987); Nishimura, Y. et al., Canc. Res. 47:999-1005 (1987); Wood, C. R. et al., Nature 314:446-449 (1985)); Shaw et al., J. Natl. Cancer Inst. 80:1553-1559 (1988); all of which references are incorporated herein by reference). General reviews of "humanized" chimeric antibodies are provided by Morrison, S. L. (Science, 229:1202-1207 (1985)) and by Oi, V. T. et al., BioTechniques 4:214 (1986); which references are incorporated herein by reference).

The present invention provides humanized antibody molecules specific for peptides having an amino acid sequence RSATEEEPPNDD (SEQ ID NO: 1), DVEDSYGQQWTYEQR (SEQ ID NO: 2) or derivatives thereof. However, the invention is not limited to these sequences but applies to any sequence in which antibodies can bind resulting in cardiac positive inotropy. In accordance with the present invention, the humanized antibodies comprised antigen specific regions in which at least parts of the CDRs of the heavy and/or light chain variable regions of a human antibody (the receptor antibody) have been substituted by analogous parts of CDRs of a murine monoclonal antibody and the humanized antibody can specifically bind to the same antigen as, for example, the Jianye-2 antibody. In a preferred embodiment of the subject invention, the CDR regions of the humanized Jianye-2 is derived from rabbits as described in the examples which follow. Some of the humanized antibodies described herein contain some alterations of the acceptor antibody, i.e., human, heavy and/or light chain variable domain framework regions that are necessary for retaining binding specificity of the donor monoclonal antibody. In other words, the framework region of some embodiments the humanized antibodies described herein does not necessarily consist of the precise amino acid sequence of the framework region of a natural occurring human antibody variable region, but contains various substitutions that improve the binding properties of a humanized antibody region that is specific for the same target as the Jianye-2 or KX-1 antibodies. A minimal number of substitutions are made to the framework region in order to avoid large-scale introductions of non-human framework residues and to ensure minimal immunogenicity of the humanized antibody in humans. The donor monoclonal antibodies of the present invention Jianye-2 or KX-1 antibodies, which are specific for the rat alpha-subunit of $(Na^++K^+)$-ATPase i.e., RSATEEEPPNDD (SEQ ID NO: 1) and DVEDSYGQQWTYEQR (SEQ ID NO: 2) peptides respectively.

The humanized antibodies compositions of the invention or other therapeutic agents of the invention may be administered to a patient in a variety of ways. Preferably, the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycine and the like.

These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, e.g., from less than about 0.5%, usually at or at least about 1% to as much as 15 or 20% by weight and will be selected primarily based on fluid volumes, viscosities, etc., in accordance with the particular mode of administration selected.

Actual methods for preparing parenterally administrable compositions and adjustments necessary for administration to subjects will be known or apparent to those skilled in the art and are described in more detail in, for example, Remington's Pharmaceutical Science, 15th Ed., Mack Publishing Company, Easton, Pa. (1980), which is incorporated herein by reference.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin Remington's Pharm. Sci., 15th Ed. (Mack Publ. Co., Easton (1975)).

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon-the dosage form employed and the route of administration utilized. For any compound used in the method of the invention, the therapeutically effective dose can be estimated initially from cell culture assays.

A dose can be formulated in animal models to achieve a circulating plasma concentration range that includes the $IC_{50}$ (i.e., the concentration of the test compound, which achieves a half-maximal inhibition of symptoms) as determined in cell culture. Such information can be used to accurately determine useful doses in humans. Levels in plasma can be measured, for example, by high performance liquid chromatography. A typical daily dose for the therapeutic molecules of the invention (i.e., antibodies, peptides, vectors encoding peptides) of the present invention might range from about 1 µg/kg to about 100 mg/kg of patient body weight or more per day, depending on the factors mentioned above, preferably about 10 µg/kg/day to 10 mg/kg/day.

Pharmaceutical compositions for use in accordance with the present invention can be formulated in conventional manner using one or more physiologically acceptable carriers or excipients. Thus, the compounds and their physiologically acceptable salts and solvates can be formulated for administration by intra venous or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

The treatment can be monitored by various ways, including echography and electrocardiograms. "Electrocardiogram" refers to a graphic tracing of variations in electrical potential caused by the excitation of the heart muscle which may be detected at the body surface. "Electrocardiogram" may be abbreviated as "ECG" or "EKG". The signals may be detected by means of metal electrodes attached to the extremities and chest wall, and may then be amplified by a sensitive voltmeter such as the electrocardiograph. The ECG waveforms are generally labeled alphabetically beginning with the P wave, which represents atrial depolarization. Approximately 0.16 seconds after the onset of the P wave, the QRS waves generally appear as a result of depolarization of the ventricular muscle, which initiates contraction of the ventricles. Finally, the T wave results from repolarization of the ventricles, which represents the onset of ventricular relaxation. The duration of the "T" wave cycle time is that time in a heart cycle when it is most vulnerable to fibrillation, a condition where the cardiac muscle fiber contracts asynchronously. Electrocardiography is further described in Harrison's Principles of Internal Medicine, Thirteenth Ed., McGraw-Hill, Inc., Chapter 189, pp. 954-966 (1994), the disclosures of which are hereby incorporated herein by reference, in their entirety.

Echocardiography is the preferred method of monitoring treatment using the molecules of the invention. "Echocardiography" (Echo) uses sound waves to form a picture of the heart valves and heart muscle. The Echo machine sends sound waves to a transducer (a sound sensitive instrument) that is placed on the patient's chest. The sound waves are reflected by the heart walls (muscle) and heart valves, back to the transducer, which changes the sound into a picture. There is no special preparation for this test. Gel is applied on the patient's chest and a transducer is placed over the heart area. Heart structures are examined by changing the direction of the transducer. The sound waves cause no discomfort. When the test is completed the gel is wiped off easily. Thus, an Echo detects the changes and provides information about heart chamber size, wall motion, valve movements, and structural changes in and around the heart.

The invention also provides for vectors which are used for treating a patient suffering from or susceptible heart disease. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available.

The practice of the present invention can suitably employ, unless otherwise indicated, conventional techniques of molecular biology and the like, which are within the skill of the art. Such techniques are explained fully in the literature. See e.g., Molecular Cloning: A Laboratory Manual, (J. Sambrook et al., Cold Spring Harbor Laboratory, Cold Spring Harbor, N. Y., 1989); Current Protocols in Molecular Biology (F. Ausubel et al. eds., 1987 and updated); Essential Molecular Biology (T. Brown ed., IRL Press 1991); Gene Expression Technology (Goeddel ed., Academic Press 1991); Methods for Cloning and Analysis of Eukaryotic Genes (A. Bothwell et al. eds., Bartlett Publ. 1990); Gene Transfer and Expression (M. Kriegler, Stockton Press 1990); Recombinant DNA Methodology (R. Wu et al. eds., Academic Press 1989); PCR: A Practical Approach (M. McPherson et al., IRL Press at Oxford University Press 1991); Cell Culture for Biochemists (R. Adams ed., Elsevier Science Publishers 1990); Gene Transfer Vectors for Mammalian Cells (J. Miller & M. Calos eds., 1987); Mammalian Cell Biotechnology (M. Butler ed., 1991); Animal Cell Culture (J. Pollard et al. eds., Humana Press 1990); Culture of Animal Cells, 2nd Ed. (R. Freshney et al. eds., Alan R. Liss 1987); Flow Cytometry and Sorting (M. Melamed et al. eds., Wiley-Liss 1990); the series Methods in Enzymology (Academic Press, Inc.); Techniques in Immunocytochemistry, (G. Bullock & P. Petrusz eds., Academic Press 1982, 1983, 1985, 1989); Handbook of Experimental Immunology, (D. Weir & C. Blackwell, eds.); Cellular and Molecular Immunology (A. Abbas et al., W. B. Saunders Co. 1991, 1994); Current Protocols in Immunology (J. Coligan et al. eds. 1991); the series Annual Review of Immunology; the series Advances in Immunology; Oligonucleotide Synthesis (M. Gait ed., 1984); and Animal Cell Culture (R. Freshney ed., IRL Press 1987).

Preferred vectors for use in the present invention include viral vectors, lipid-based vectors and other vectors that are capable of delivering DNA to non-dividing cells in vivo. Presently preferred are viral vectors, particularly replication-defective viral vectors (including, for example replication-defective adenovirus vectors and adeno-associated virus (AAV) vectors. For ease of production and use in the present invention, replication-defective adenovirus vectors are presently most preferred.

"Gene delivery," "gene transfer," and the like as used herein, are terms referring to the introduction of an exogenous polynucleotide (sometimes referred to as a "transgenes") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein. Targeted vectors include vectors (such as viruses, non-viral protein-based vectors and lipid-based vectors) in which delivery results in transgene expression that is relatively limited to particular host cells or host cell types. By way of illustration, therapeutic molecules, for example, nucleic acid sequences encoding for the peptides of the invention, to be delivered to a patient can be operably linked to heterologous tissue-specific promoters thereby restricting expression to cells in that particular tissue.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

The presently preferred means of in vivo delivery, is by injection of the vector into a blood vessel directly supplying the myocardium, preferably by injection into a coronary artery. Such injection is preferably achieved by catheter introduced substantially (typically at least about 1 cm) within the ostium of one or both coronary arteries or one or more saphenous veins or internal mammary artery grafts or other conduits delivering blood to the myocardium.

By injecting the vector stock, preferably containing no wild-type virus, deeply into the lumen of one or both coronary arteries (or grafts and other vascular conduits), preferably into both the right and left coronary arteries (or grafts and other vascular conduits), and preferably in an amount of about $10^7$-$10^{13}$ viral particles as determined by optical densitometry (more preferably $10^9$-$10^{11}$ viral particles), it is possible to locally transfect a desired number of cells, especially cardiac myocytes, with genes that encode proteins that regulate cardiac contraction, such as, for example, the peptides discussed infra, thereby maximizing therapeutic efficacy of gene transfer, and minimizing undesirable effects at extracardiac sites and the possibility of an inflammatory response to viral proteins. Vector constructs that are specifically targeted to the myocardium, such as vectors incorporating myocardial-specific binding or uptake components, and/or which incorporate inotropic molecules, for example, the peptides described above, that are under the control of myocardial-specific transcriptional regulatory sequences (e.g., ventricular myocyte-specific promoters) can be used in place of or, preferably, in addition to such directed injection techniques as a means of further restricting expression to the myocardium, especially the ventricular myocytes. For vectors that can elicit an immune response, it is preferable to inject the vector directly into a blood vessel supplying the myocardium as described above, although the additional techniques for restricting the potential for extracardiac expression can also be employed.

Additional references describing cell types found in the blood vessels, and the structure of the vasculature which may be useful in the methods of the present invention include the following: W. Bloom & D. Fawcett, A Textbook of Histology, 10th Ed., (W. B. Saunders Co. 1975). Methods of uses of gene transfer for the treatment or prevention of disease, including heart disease are described, e.g., Methods in Molecular Biology, Vol. 7: Gene Transfer and Expression Protocols, Murray, E. (ed.), Humana Press, Clifton, N.J. (1991); Mazur et al., Molecular and Cellular Pharmacology, 21:104-111, 1994; French, Herz 18:222-229, 1993; Williams, American Journal of Medical Sciences 306:129-136, 1993; and Schneider and French, Circulation 88:1937-1942, 1993.

"Vasculature" or "vascular" are terms referring to the system of vessels carrying blood (as well as lymph fluids) throughout the mammalian body.

"Blood vessel" refers to any of the vessels of the mammalian vascular system, including arteries, arterioles, capillaries, venules, veins, sinuses, and vasa vasorum.

"Artery" refers to a blood vessel through which blood passes away from the heart. Coronary arteries supply the tissues of the heart itself, while other arteries supply the remaining organs of the body. The general structure of an artery consists of a lumen surrounded by a multi-layered arterial wall.

The invention also provides for methods for identifying peptides and antibodies which are positive inotropic agents. To prepare an antibody that specifically binds to a region of the ($Na^+$+$K^+$)-ATPase, purified peptides or their nucleic acid sequences representing the different subunits of ($Na^+$+$K^+$)-ATPase can be used. Using purified peptides or their nucleic acid sequences representing the different subunits of ($Na^+$+$K^+$)-ATPase, antibodies that specifically bind to a desired peptide can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). Such techniques include, but are not limited to, antibody preparation by selection of antibodies from libraries of recombinant antibodies in phage or similar vectors, as well as preparation of polyclonal and monoclonal antibodies by immunizing animals (see, e.g., Huse et al., Science 246:1275-1281 (1989); Ward et al., Nature 341:544-546 (1989)); humanized antibodies; production of antibodies by any of the methods discussed above. After the antibody is provided, the specificity of the antibody can be detected using any of suitable immunological binding assays known in the art (see, e.g., U.S. Pat. Nos. 4,366,241; 4,376,110; 4,517,288; and 4,837,168). Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra.

To determine whether these identified antibodies are positive inotropic agents, standard assays such as those described in the Examples which follow can be used. For example, measurement of cell contraction assays; confocal $Ca^{2+}$ imaging; $(Na^++K^+)$-ATPase activity assays and the like.

In another embodiment peptides that induce production of inotropic antibodies in vivo and in vitro are preferred. The peptides can be individual peptides, peptides co-administered with adjuvants, peptides coupled to peptides with different amino acid sequences and/or the same peptides coupled to each other as repeating units. Also, while peptides may be directly coupled to each other, in some cases a small linker sequence or a larger heterolinker molecule may be advantageously used to couple the two peptides. For example, as the spacer, one or a few, up to about 5, preferably, up to about 3, neutral amino acids, such as glycine, may be used to link the peptides. A preferred spacer peptide is GGG, however, the spacer may be made larger or smaller and altered to include other molecules besides the amino acid glycine. As examples of heterolinkers may be made of, for example, N-succinimidyl-3-(2-pyridylthi-o) propinate (SPDP), m-maleimidobenzoyl-N-hydroxy-succimide (MBS) as well as any of the other reagents employed to link peptides. When the peptides are not directly bonded the linking group will generally and preferably be any divalent linking group. The linking group may be cleavable or non-cleavable under physiological conditions or by appropriate inducement.

Although the total number of amino acids in the conjugated polypeptide is not particularly critical, from a practical aspect, the minimum number of amino acids, including any amino acid spacers or linkers, will generally be at least about 10 or 12, preferably at least about 20, to obtain adequate antigen presentation and immunogenicity up to about 100 amino acids.

The polypeptides of this invention may be used as a vaccine either prophylactically or therapeutically. When provided prophylactically the vaccine is provided in advance of any evidence of muscular contractile disorders. Antibodies are produced against the peptides which are inotropic. The prophylactic administration of the invention vaccine should serve to prevent or attenuate, for example cardiac muscle contractile disorders. In a preferred embodiment a human, at high risk for heart muscle contractile disorders is prophylactically treated with a vaccine of this invention. When provided therapeutically, the vaccine is provided to enhance the patient's own antibody response to produce the desired inotropic antibodies.

While it is possible for the immunogenic polypeptide, which may or may not be conjugated, to be administered in a pure or substantially pure form, it is preferable to present it as a pharmaceutical composition, formulation or preparation.

The formulations of the present invention, both for clinical and for human use, comprise a conjugated polypeptide as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

In general, the formulations are prepared by uniformly and intimately bringing into association the active ingredient with liquid carriers or finely divided solid carriers or both, and then, if necessary, shaping the product into the desired formulation.

Formulations suitable for any route of administration may be used, such as, for example, intravenous, intramuscular, subcutaneous, intraperitoneal, nasal, oral, rectal, vaginal, etc. Generally, the formulations will comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1-2.0M), glycine, and the like, and having a buffered pH compatible with physiological conditions to produce an aqueous solution, and rendering the solution sterile. These may be present in unit or multi-dose containers, for example, sealed ampoules or vials.

The formulations of the present invention may incorporate a stabilizer. Illustrative stabilizers include polyethylene glycol, proteins, saccharides, amino acids, inorganic acids, and organic acids which may be used either on their own or as admixtures. These stabilizers, when used, are preferably incorporated in an amount of about 0.1 to about 10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of about 0.1 to about 3.0 osmoles, preferably in the range of about 0.3 to about 1.2. The pH of the aqueous solution is adjusted to be within the range of about 5.0 to about 9.0, preferably within the range of 6-8. In formulating the immunogen of the present invention, anti-adsorption agent may be used.

Additional pharmaceutical methods may be employed to control the duration of action. Controlled release preparations may be achieved through the use of polymer to complex or absorb the conjugated polypeptide. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the conjugated polypeptide into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacrylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc, magnesium stearate, crystalline cellulose, methyl cellulose, carboxymethyl cellulose, glycerin, sodium alginate or gum arabic among others. These carriers may likewise be used for preparing to be administered via other cavities, e.g., nasal, rectal, etc.

The conjugated polypeptides of the present invention may be supplied in the form of a kit, alone, or in the form of a pharmaceutical composition as described above.

As noted above, the administration of the vaccine of the present invention may be for either a prophylactic or therapeutic purpose. When provided therapeutically, the immunogen is provided at (or after) the onset of the disease or at the onset of any symptom of the disease. The therapeutic administration of the immunogen serves to attenuate the disease.

The present invention, therefore, provides antigenic conjugated polypeptides, which provide powerful vaccines for eliciting immune responses for production of inotropic antibodies in vivo.

The conjugated polypeptides, which may be prepared by conventional solid phase peptide synthesis or other conventional means for peptide synthesis, however, the peptides may also be prepared by genetic engineering techniques. The DNA sequences coding for the peptides of this invention can be prepared by any of the well known techniques for recombinant gene technology. For example, reference can be made to the disclosure of recombinant proteins and peptides in U.S. Pat. No. 5,142,024 and the body of literature mentioned therein, the disclosures of which are incorporated herein by reference thereto.

The following non-limiting examples are illustrative. All documents mentioned herein are hereby incorporated by reference.

EXAMPLES

In the following examples, the following materials and methods were employed.

Materials and Methods

Materials.

All reagents were purchased from Sigma Chemical Co., unless specified.

Highly purified dog kidney $(Na^+ + K^+)$-ATPase was a gift from Dr. Jack Kyte.

Antibody Preparation.

The RSATEEEPPNDD (SEQ ID NO:1) and DVEDSYGQQWTYEQR (SEQ ID NO:2) peptides were synthesized according to the protein sequence reported (Schneider, J. W., Mercer, R. W., Caplan, M., Emanuel, J. R., Sweadner, K. J., Benz, E. J., Levenson, R. (1985) Proc. Natl. Acad. Sci. U.S.A. 82, 6357-6361; Xie, Z., Li, H., Liu, G., Wang, Y., Askari, A., Mercer, R. W. (1994) Cloning of the dog Na/K-ATPase alpha 1 subunit. The Na Pump. (Bamberg, S., and Schoner, W., Eds), pp. 49-52, Springer-Verlag, New York, N.Y.; Shull, M. M., Lingrel, J. B. (1987) Proc. Natl. Acad. Sci. U.S.A. 84, 4039-4043). The polyclonal Jianye antibody was generated in New Zealand White rabbits using KLH as a peptide carrier (Genemed). The immunoglobulins (IgG) were purified through an affinity column directed against the same synthetic peptide of the $(Na^+ + K^+)$-ATPase. Purified antibodies recognize both denatured (by Western blots) and native $(Na^+ + K^+)$-ATPase (by immunocytostaining). Synthetic peptides were also utilized as the specific peptide blockers for the antibodies.

Isolation of Cardiac Myocytes:

Ventricular cardiac myocytes were isolated from adult Sprague-Dawley rats (2-3 months old; weight 225-300 g) using standard enzymatic techniques. Briefly, following anesthesia (sodium pentobarbital, 100 mg/kg), the heart was quickly removed from the chest and aortic perfused at constant pressure (100 cmH$_2$O) at 37° C. for 3 minutes with a $Ca^{2+}$-free bicarbonate-based buffer containing 120 mM NaCl, 5.4 mM MgSO$_4$, 1.2 mM NaH$_2$PO$_4$, 5.6 mM glucose, 20 mM NaHCO$_3$, and 5 mM taurine, in the presence of O$_2$ (95%)-CO$_2$ (5%). The enzymatic digestion was initiated by adding collagenase (Worthington Type II, 1 mg/ml) to the perfusion solution. Calcium (50 μM) was added to the enzyme solution when the heart became swollen. About 7 minutes later, the left ventricle was quickly removed, cut into several pieces, and further digested on a shaker (60-70 rpm) for 10 minutes in the same enzyme solution. The supernatant containing the dispersed myocytes was filtered into a test tube and gently centrifuged at 500 rpm for 1 minute. The cell pellet was then promptly resuspended in a solution containing 0.125 M $Ca^{2+}$. The supernatant was aspirated after the myocytes were pelleted by gravity for 10 minutes and the myocytes were then resuspended in a solution containing 0.25 mM $Ca^{2+}$. The shake-harvest procedure was repeated several times until all of the pieces were digested. For freshly isolated cells, myocytes were suspended in HEPES-buffer consisting of 1 mM CaCl$_2$, 0.137 mM NaCl, 5.4 mM KCl, 15 mM dextrose, 1.3 mM MgSO$_4$, 1.2 mM NaH$_2$PO$_4$, and 20 mM HEPES, pH 7.4.

Measurement of Mice Cardiac Contraction In Vivo:

Male wild-type mice (CD1, Charles River, 32-40 g) were utilized for this study. Mice In vivo cardiac functions were assessed by pressure-volume catheter in anesthetized mice. Briefly, mice were induced with 5% isofluorane, anesthetized with an intraperitoneal injection of urethane (300-500 mg/kg), etomidate (5 mg/kg) and morphine (0.5 mg kg$^{-1}$), and intubated with a blunt 19G needle inserted via tracheostomy. Additional small dose was given when increase in heart rate or blood pressure was observed in response to tail pinch with forceps. Ventilation was initiated with 100% oxygen using a custom-designed, constant flow ventilator delivering a tidal volume of 6.7 μL/kg at 120 breaths per min. The left external jugular vein was cannulated with a 30G needle connected to an infusion pump. Modest volume expansion was provided (150 μL of 12.5% human albumin) at 50 μL/min. Following stabilization, a lateral incision was made at the xyphoid cartilage to expose the left ventricular (LV) apex. The 1.4 F pressure-volume catheter (SPR-839, Millar Instruments Inc., Houston, Tex., USA) was inserted via an apical needle puncture with a 26G needle, and advanced along the cardiac long axis. A 2F pacing catheter (NuMed, Nicholville, N.Y., USA) was placed in the esophagus, dorsal to the left atrium. Atrium was paced using 5-7 V, 2 ms pulses (SD25, Grass Instruments, Quincy, Mass., USA). Calibration of the volume signal was performed using a 5-10 μL bolus of 30% hypertonic saline injected into the jugular vein to determine the signal offset and ultrasound flow probe (AT01RB, Transonic Systems Inc.) placed around the thoracic aorta to determine signal gain. Data were digitized at 2 kHz and stored to disk for off line analysis.

Mice cardiac atria pacing were maintained at constant beating (600 beats/min). The hearts were infused with PBS (5 l/min) for 10 min prior for administration of SSA78 infusion (5 μl/min) for 30 minutes and following by 10 min PBS washout at 5 μl/imin. Control experiments showed that the vehicle (PBS), at the experimental infusion rates, has no effect on cardiovascular performance. Indices of myocardial systolic and diastolic performance were derived from pressure-volume data obtained both at steady-state (every minute) and during transient loading of the heart with direct occlusion of the inferior vena cava (IVC) (every 5 minutes). Steady-state indices were derived from 10 consecutive averaged beats. Cardiac preload was indexed as the left ventricular end-diastolic volume (EDV) and end-diastolic pressure (EDP). Cardiac afterload was evaluated as effective arterial elastance (Ea; ratio of LV systolic pressure to stroke volume). This parameter is not preload dependent and had been validated to closely approximate total afterload, which incorporates systemic vascular resistance, aortic impedance, and the reflected wave properties of the vasculature. Myocardial contractility was indexed by cardiac output (CO), dPdt max, dPdt max normalized to instantaneous developed pressure (dPdt max/IP), the load-independent end-systolic pressure-volume relationship (Ees) and preload recruitable stroke work (PRSW). Diastolic performance was measured by dPdt min and the time constant of ventricular relaxation.

Measurement of Cell Contraction

Cardiac myocytes were isolated from wild-type adult Sprague-Dawley rats, using a standard enzymatic method described previously (Xu, K. Y., et al., (2002) BBRC, 289:167-172). Isolated myocytes were suspended in a buffer containing (in mM) 137 NaCl, 5.4 KCl, 15 dextrose, 1.3 MgSO$_4$, 1.2 NaH$_2$PO$_4$, 1 CaCl$_2$, and 20 HEPES, pH 7.4. To measure cell contractility, cardiac myocytes were placed on an inverted microscope (Zeiss model IM-35), bathed with a HEPES-buffered solution, and electrically stimulated under 0.5 Hz at room temperature. The designated reagents were added when the baseline contraction was stabilized after 10-15 min constant pacing. Cell length was monitored from the bright-field image (650 nm to 750 nm red light illumination) by an optical edge-tracking method using a photodiode array (model 1024 SAQ, Reticon) with a 3-ms time resolution. The contraction amplitude was indexed by the percentage shortening of cell length.

Measurement of Intracellular $Ca^{2+}$ Transients

Rat cardiac myocytes were loaded with 50 µg of a cell permeable fluorescent $Ca^{2+}$ probe, Indo-1/acetoxymethylester (Indo-1/AM, Molecular Probes, Inc., Eugene, Oreg.) for 10 min and then resuspended in HEPES-buffered solution in the presence of 1 mM $Ca^{2+}$ and stored in the dark at room temperature for 60 min before be utilized for the experiments. The Indo-1 loaded cells were placed on the stage of a modified inverted microscope (model IM-35; Carl Zeiss, Inc., Thornwood, N.Y.) equipped for simultaneous recording of Indo-1 flrorescence and cell length. Cells were electrically paced at 0.5 Hz at room temperature and the excitation wavelength was selected by a 350-nm interference filter (bandwidth 10 nm; Oriel Corp., Stratford, Conn.). The ratio of emission intensity at 410 nm to that at 490 nm was computed offline as an index of intracellular $Ca^{2+}$ ($Ca_i^{2+}$) transient. The peak amplitude of the transient is defined as the difference of the 410:490 fluorescence ratio before and after electrical stimulation with or without antibody.

Isolation of Sarcolemmal Vesicles and Purification of $(Na^++K^+)$-ATPase:

Rat cardiac sarcolemmal (SL) vesicles were isolated from rat heart muscle by sucrose flotation method. The vesicles were tested with saponin and were predominately right-side-out in orientation. $(Na^++K^+)$-ATPase was purified as described previously (Kyte, J. (1971) Biochemistry, 246: 4157-4165). Briefly, the SL vesicles (4.4 mg/ml) were titrated with 0.58 mg/ml of SDS in the presence of 2 mM ATP at 20.degree. C. for 30 min. The SDS titrated fractions were then loaded on the top of a sucrose (W/W) step gradient constructed with 10 ml of 37.3% (bottom step), 20 ml of 28.8%, and 10 ml of 15% in a Ti 60 tube, and centrifuged at 40,000 rpm for 90 min. The fractions that contain $(Na^++K^+)$-ATPase (between 37.3 and 28.8% on the sucrose gradient) were carefully collected and sedimented at 40,000 rpm for 60 minutes. The purified enzyme was resuspended in a sucrose (250 mM)/histidinium chloride (30 mM) buffer, pH 7.2, quick-frozen in liquid nitrogen and stored at 70.degree. C. Highly purified dog kidney $(Na^++K^+)$-ATPase was a gift from Dr. Jack Kyte.

Determination of $(Na^++K^+)$-ATPase Activity:

The enzymatic activity was determined as described previously (Kyte J., et al., (1987) Biochemistry, 26:8350-8360) with modifications. Briefly, purified rat or dog $(Na^++K^+)$-ATPase was incubated with or without Jianye or ouabain in the presence of 100 mM Na.+ for 30 min at room temperature. The reaction was initiated by adding 3 mM MgATP and 20 mM $K^+$ in a final volume of 0.25 ml at 37° C. for 30 min and terminated by adding 0.75 ml quench solution and 0.025 ml developer. The color was allowed to develop for 30 min at room temperature and the concentration of phosphate was then determined at 700 nm using a spectrophotometer.

Echocardiography

Echocardiography (Echo) uses sound waves to form a picture of the heart valves and heart muscle. The Echo machine sends sound waves to a transducer (a sound sensitive instrument) that is placed on the animal's chest. The sound waves are reflected by the heart walls (muscle) and heart valves and back to the transducer, which changes the sound into a picture. Gel is applied on the rat chest and a transducer is placed over the heart area. Heart structures are examined by changing the direction of the transducer. The sound waves cause no discomfort. Thus, an Echo detects the changes and provides information about heart chamber size, wall motion, valve movements, and structural changes in and around the heart.

Example 1

Jianye-2 Inotropic Antibody

Figure 2:
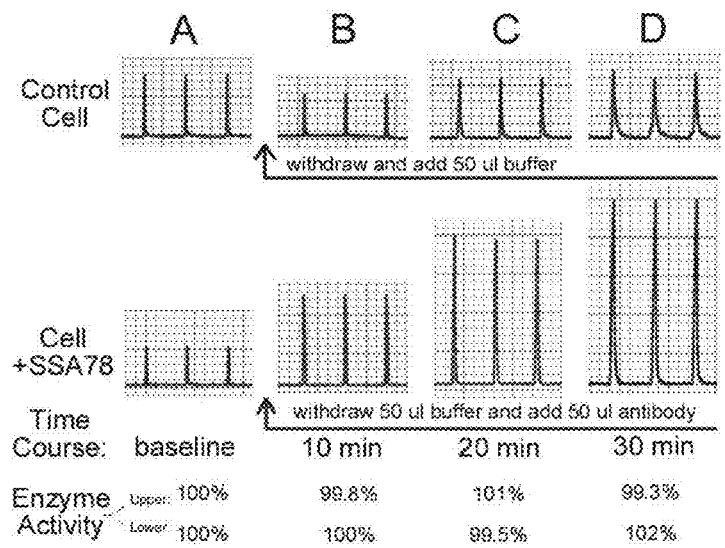
FIG. 2 presents electrocardiograms showing results of the time course of rat heart cell contraction with or without Jianye-2 antibody. Time runs from left to right. Column A, shows the baselines of rat heart cell contraction. Columns B, C, D show the results obtained 10, 20, 30 min after administration of either buffer (upper panel) or Jianye-2 antibody (lower panel). Enzyme activity was monitored in cell homogenates under the same experimental condition. The results show that Jianye-2 antibody enhanced rat heart cell contraction without inhibiting $(Na^++K^+)$-ATPase activity.
Figure 3:
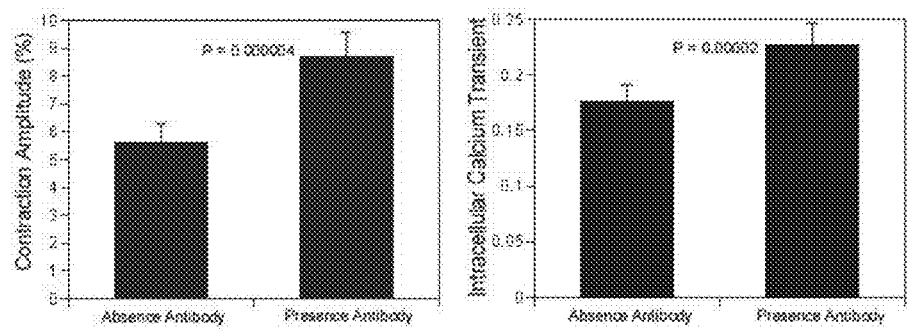
FIG. 3 shows that Jianye-2 antibody markedly increased intracellular $Ca^{2+}$ contraction and demonstrates that intracellular $Ca^{2+}$ concentration is involved in the mechanisms of Jianye-2 antibody enhanced heart cell contraction. The data represent a mean of 12 independent experiments.
Figure 4:
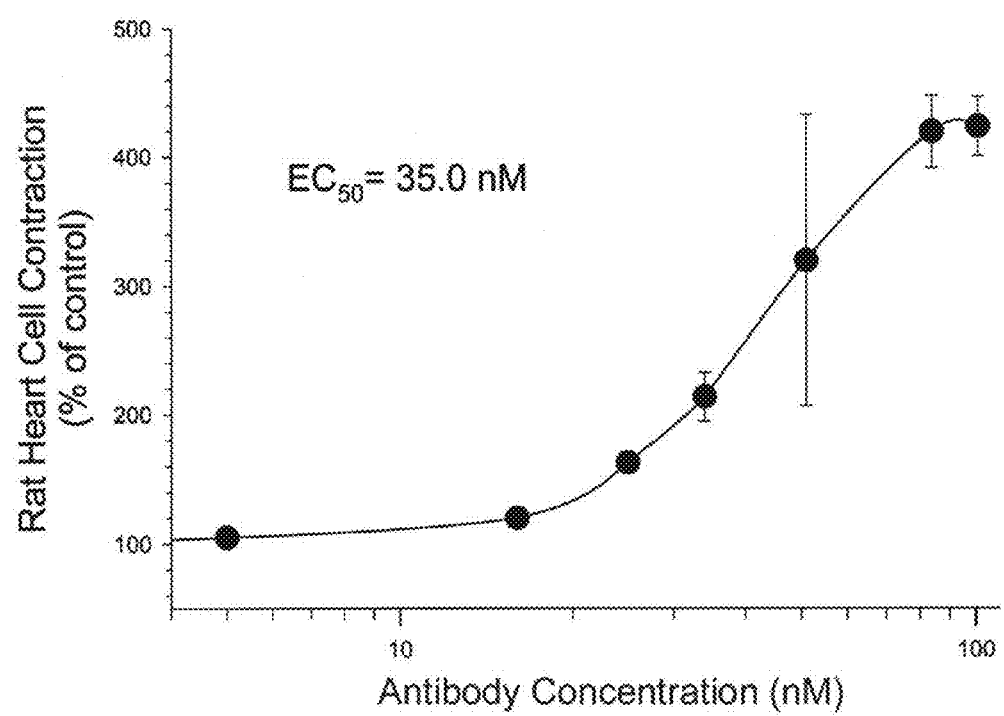
FIG. 4 is the dose-dependent contractile response of Jianye-2 antibody in rat ventricular myocytes. The half maximal contractile response (EC50) is 35 nM. The data represent a mean of four independent experiments.

Jianye-2 antibody, which specifically recognizes the RSATEEEPPNDD (SEQ ID NO:1) peptide of the alpha-subunit of the $(Na^++K^+)$-ATPase, has been found to increase the contractility of isolated rat ventricular myocytes. FIG. 1 shows the results obtained with immunofluorescent staining of Jianye-2 antibody in rat cardiac myocytes and African green monkey CV-1 cells. Confocal image of rat cardiac myocytes in the presence of Jianye-2, shown in FIG. 1A or with both Jianye-2 antibody and peptide blocker (FIG. 1B). FIG. 1C shows the immunofluorescent stainings of Jianye-2 antibody in a group of CV-1 cells at a magnification of 400.times. FIG. 1D shows the CV-1 cell image at 3000 times. Jianye-2 antibody staining in the presence of either 1 mM ouabain (FIG. 1E) or strophanthidin (FIG. F). The results reveal that ouabain and strophanthidin compete with the Jianye-2 antibody binding site indicating that Jianye-2 antibody specifically binds to the $(Na^++K^+)$-ATPase on the extracellular surface of the cell membrane. FIG. 2 shows results of the time courses of rat heart cell contraction with or without Jianye-2 antibody. Time runs from left to right. Column A, shows the baselines of rat heart cell contraction. Columns B, C, D show the results obtained 10, 20, 30 min after administration of either buffer (upper panel) or Jianye-2 antibody (lower panel, 85 nM). Enzyme activity was monitored in cell homogenates under the same experimental condition. The results show that Jianye-2 antibody enhanced rat heart cell contraction without inhibiting $(Na^+$ $K^+$)-ATPase activity. FIG. 3 shows that Jianye-2 antibody markedly increased intracellular $Ca^{2+}$ contraction and demonstrates that intracellular $Ca^{2+}$ concentration is involved in the mechanisms of Jianye-2 antibody enhanced heart cell contraction. The data represent a mean of 12 independent experiments. FIG. 4 shows the dose-dependent contractile response of Jianye-2 antibody in rat ventricular myocytes. The half maximal contractile response (EC50) is 35 nM. The data represent a mean of four independent experiments.

Figure 5:
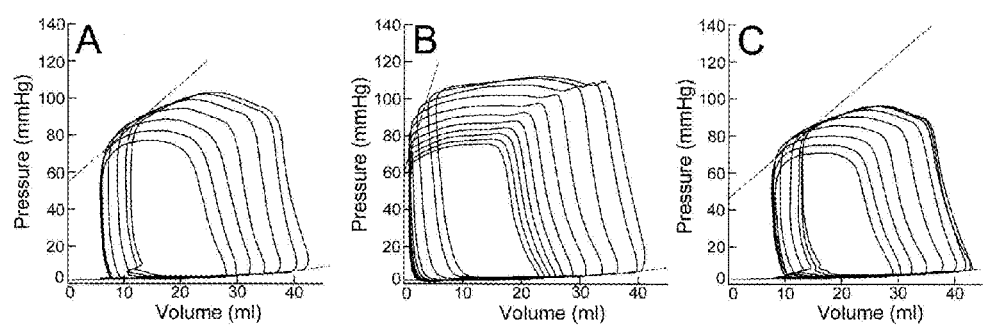
FIG. 5 is a schematic representation of pressure-volume loops of the effect of Jianye-2 antibody on normal mouse heart left ventricle. Jianye-2 antibody (total 150 ml, 6.0 µM in PBS, pH 7.2) was administered to the mouse heart at a rate of 5 ml/min. The results show that Jianye-2 antibody dramatically induced a reversible positive inotropic effect as demonstrated by the changes in ventricular pressure-volume loops with time during the cardiac cycle. The results represent one of the seven similar experiments.
Figure 6:
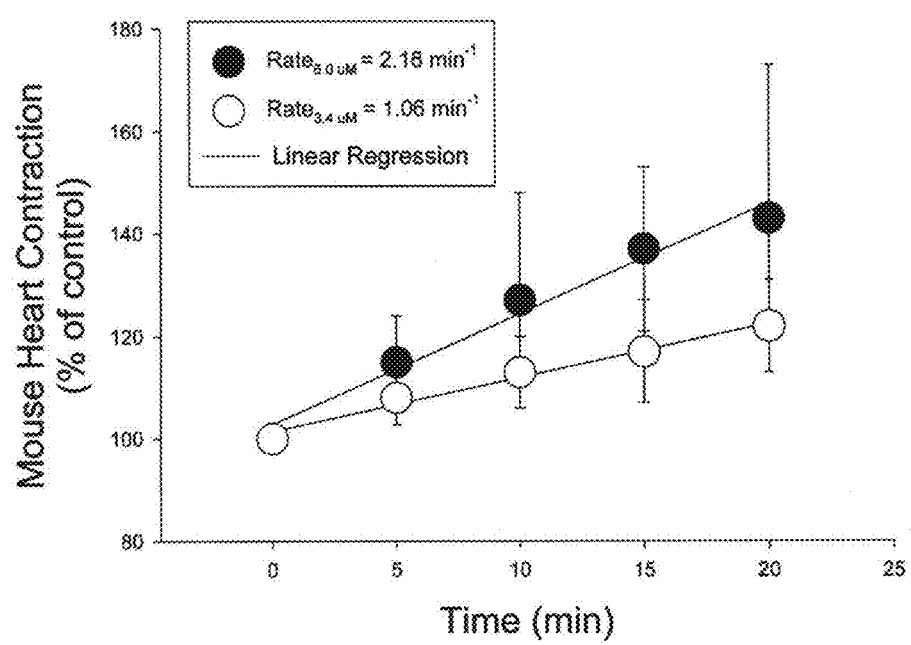
FIG. 6 shows the time- and concentration-dependent Jianye-2 antibody effects on mouse heart contraction in vivo mouse model. At different fixed concentrations of Jianye-2 antibody as indicated in the figure, the data are plotted in the form of percent of mouse heart contraction as a function of time. Compared with the background control (at 0 min as 100%), Jianye-2 antibody increased mouse heart contractions are expressed as percentages (%) for 5, 10, 15, and 20 min respectively after administration of 3.4 µM (open circles) or 6.0 µM (black circles) of Jianye-2 antibody. Mouse heart contraction was 108(±5.3), 113(±7), 116(±10), 122(±9.0) as shown in the open circles, and 115(±9.0), 127(±21), 137(±16), and 143(±30) in black circles. First order rate constants were 1.06 and 2.16%/min for 3.4 µM and 6.0 µM Jianye-2 antibody, respectively. The data represent the mean of 5 independent determinations.
Figure 7:
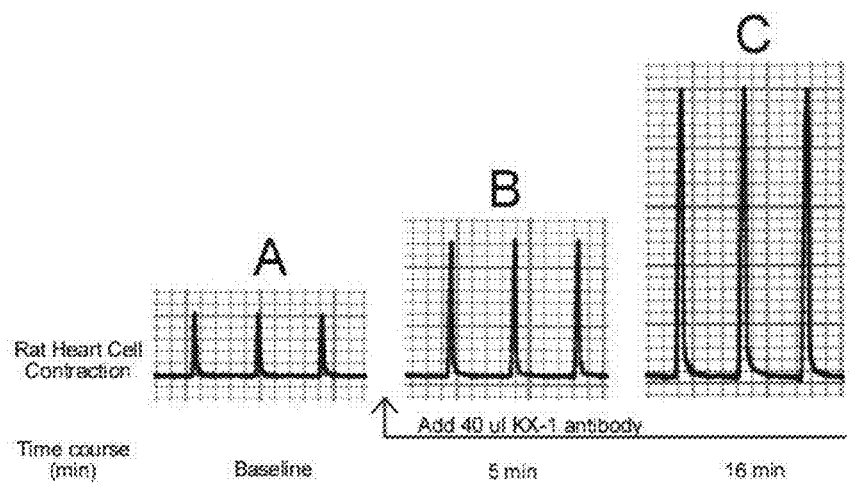
FIG. 7 shows that the KX-1 antibody enhanced the velocity of shortening of rat ventricular myocyte and increased the force of contraction of the heart cells. Time runs from left to right. Column A represents the baselines of rat heart cell contraction. Columns B & C: 5 and 16 minutes following administration of KX-1. The final concentration of KX-1 was 0.74 µM. The results indicate that the KX-1 antibody is an inotropic agent.

FIG. 5 is a schematic representation of pressure-volume loops of the effect of Jianye-2 antibody on normal mouse heart left ventricle. Jianye-2 antibody (total 150 ml, 6.0 µM in PBS, pH 7.2) was administered to the mouse heart at a rate of 5 ml/min. The results show that Jianye-2 antibody dramatically induced a reversible positive inotropic effect as demonstrated by the changes in ventricular pressure-volume loops with time during the cardiac cycle. The results represent one of the seven similar experiments. FIG. 6 shows the time- and concentration-dependent Jianye-2 antibody effects on mouse heart contraction in vivo model. At different fixed concentrations of Jianye-2 antibody as indicated in the figure, the data are plotted in the form of percent of mouse heart contraction as a function of time. Compared with the subunit of the ($Na^+$+$K^+$)-ATPase, has been found to increase the contractility of isolated rat heart cells. Vaccination of its specific peptide-antigen in heart diseased animal model significantly decreased the progression of heart failure. This KX-1 antibody, its peptide vaccine, and monoclonal and humanized antibodies are useful for treatment of heart failure and other contractile disorders. FIG. 7 shows that the KX-1 antibody enhanced the velocity of shortening of rat ventricular myocyte and increased the force of contraction of the heart cells. The results indicate that the KX-1 antibody is an inotropic agent.

Figure 8:
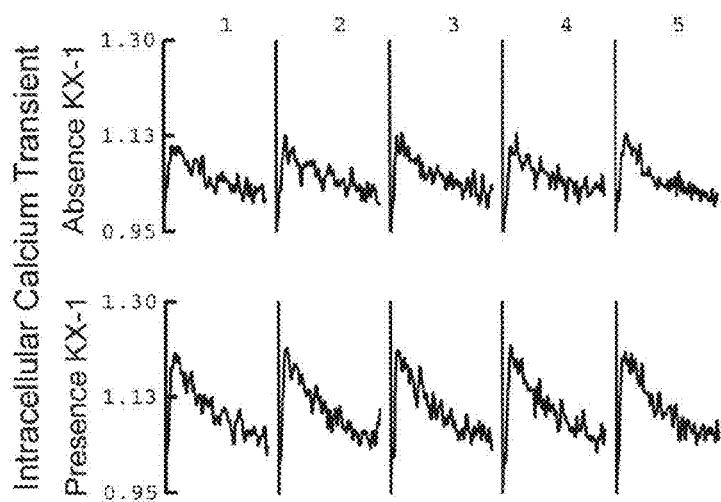
FIG. 8 represents the changes of intracellular calcium transient following the binding of KX-1 to the $(Na^++K^+)$-ATPase and indicates that KX-1 induced heart cell contraction is dependent on intracellular $Ca^{2+}$ increase.
Figure 9:
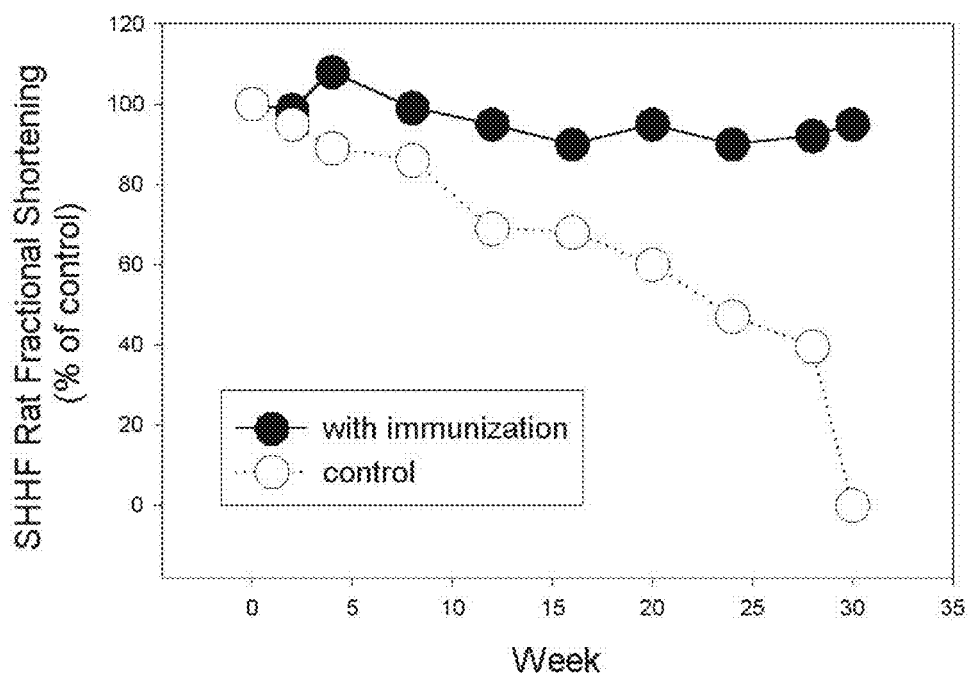
FIG. 9 is a graph showing the effect of immunization with KX-1 on the rat cardiac heart failure function. The peptide DVEDSYGQQWTYEQR (SEQ ID NO: 2) was injected into the animal as a vaccine to reduce the rate of progression of heart failure in the heart failure rat model. TiterMax Gold was used as an adjuvant throughout the experiment. The results show that endogenous KX-1 antibody generation significantly delayed the rate of the progression of heart failure in heart failure rats (black circles). In contrast, cardiac function was significantly depressed in the control heart failure rat without immunization with KX-1 antigen (open circles).

FIG. 8 represents the changes of intracellular calcium transient following the binding of KX-1 to the ($Na^+$+$K^+$)-ATPase and indicates that KX-1 induced heart cell contraction is dependent on intracellular $Ca^{2+}$ increase. FIG. 9 reveals that the DVEDSYGQQWTYEQR (SEQ ID NO:2) peptide can be utilized as a vaccine to generation of endogenous KX-1 antibody in heart failure rats and the results show that endogenous KX-1 antibody delayed the rate of progression of heart failure in live heart failure rat animal models. In contrast, cardiac function was significantly depressed in the control heart failure rat without immunization with KX-1 antigen.

SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide

<400> SEQUENCE: 1

Arg Ser Ala Thr Glu Glu Glu Pro Pro Asn Asp Asp
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Asp Val Glu Asp Ser Tyr Gly Gln Gln Trp Thr Tyr Glu Gln Arg
1               5                   10                  15 background control (at 0 min as 100%), Jianye-2 antibody increased mouse heart contractions are expressed as percentages (%) for 5, 10, 15, and 20 min respectively after administration of 3.4 mM (open circles) or 6.0 mM (black circles) of Jianye-2 antibody. Mouse heart contraction was 108(±5.3), 113(±7), 116(±10), 122(±9.0) as shown in the open circles, and 115(±9.0), 127(±21), 137(±16), and 143 (±30) in black circles. First order rate constants were 1.06 and 2.16%/min for 3.4 mM and 6.0 mM Jianye-2 antibody, respectively. The data represent the mean of 5 independent determinations.

Example 2

KX-1 Inotropic Antibody

Antibody (KX-1), which recognizes DVEDSYGQQWTYEQR (SEQ ID NO:2) peptide of alpha-

What is claimed is:

1. A method of producing a positive inotropic effect in a mammalian host comprising administering to said mammalian host a therapeutically effective amount of a synthetic peptide consisting of the amino acid sequence of DVEDSYGQQWTYEQR (SEQ ID NO:2), wherein an endogenous antibody is generated through the synthetic peptide antigen and the endogenous antibody binds ($Na^+$+$K^+$)-ATPase to increase intracellular calcium, wherein the endogenous antibody enhances the velocity of shortening of the ventricular myocyte and increases the force of contraction of the heart cells, wherein the mammalian host suffers from a heart disease in need of an enhancement of the velocity of shortening of the ventricular myocyte and an increase in the force of contraction of the heart cells.

2. The method of claim 1, wherein the peptides, or their derivatives or isoforms, administered individually or in combination with one or more pharmaceutically acceptable carrier to the host.

3. The method of claim 1, wherein the method further comprise monitoring the mammal's cardiac contractions for a positive inotropic effect.

\* \* \* \* \*